United States Patent [19]
Ottieri et al.

[11] Patent Number: 5,268,000
[45] Date of Patent: Dec. 7, 1993

[54] INTRAMEDULLARY NAIL

[76] Inventors: Marco T. Ottieri, Via E. Manfredi, 9 (00197)-Roma, Italy; Francesco S. Santori, Via Ronciglione, 9 (00191)-Roma, Italy

[21] Appl. No.: 945,104
[22] Filed: Sep. 15, 1992
[51] Int. Cl.⁵ .............................................. A61B 17/56
[52] U.S. Cl. ........................................ 606/62; 606/63; 606/67; 606/68
[58] Field of Search ............... 606/62, 63, 64, 65, 606/66, 67, 68

[56] References Cited

U.S. PATENT DOCUMENTS

| | | | |
|---|---|---|---|
| 2,381,050 | 8/1945 | Hardinge | 606/65 |
| 3,216,414 | 11/1965 | Street | 606/68 |
| 4,632,101 | 12/1986 | Freedland | 606/68 |
| 4,827,917 | 5/1989 | Brumfield | 606/66 |
| 5,057,103 | 10/1991 | Davis | 606/68 |
| 5,098,433 | 3/1992 | Freedland | 606/68 |
| 5,112,333 | 5/1992 | Fixel | 606/62 |
| 5,116,335 | 5/1992 | Hannon | 606/62 |
| 5,122,141 | 6/1992 | Simpson | 606/64 |

Primary Examiner—Michael A. Brown
Attorney, Agent, or Firm—Paul J. Cook

[57] ABSTRACT

An intramedullary nail is provided having a top end and a distal end. Pivotally mounted jaws are located at the distal end which, when closed, are adapted to be secured about fixed supports in a fractured bone to be healed. The jaws can be fixed into position about the fixed supports.

11 Claims, 5 Drawing Sheets

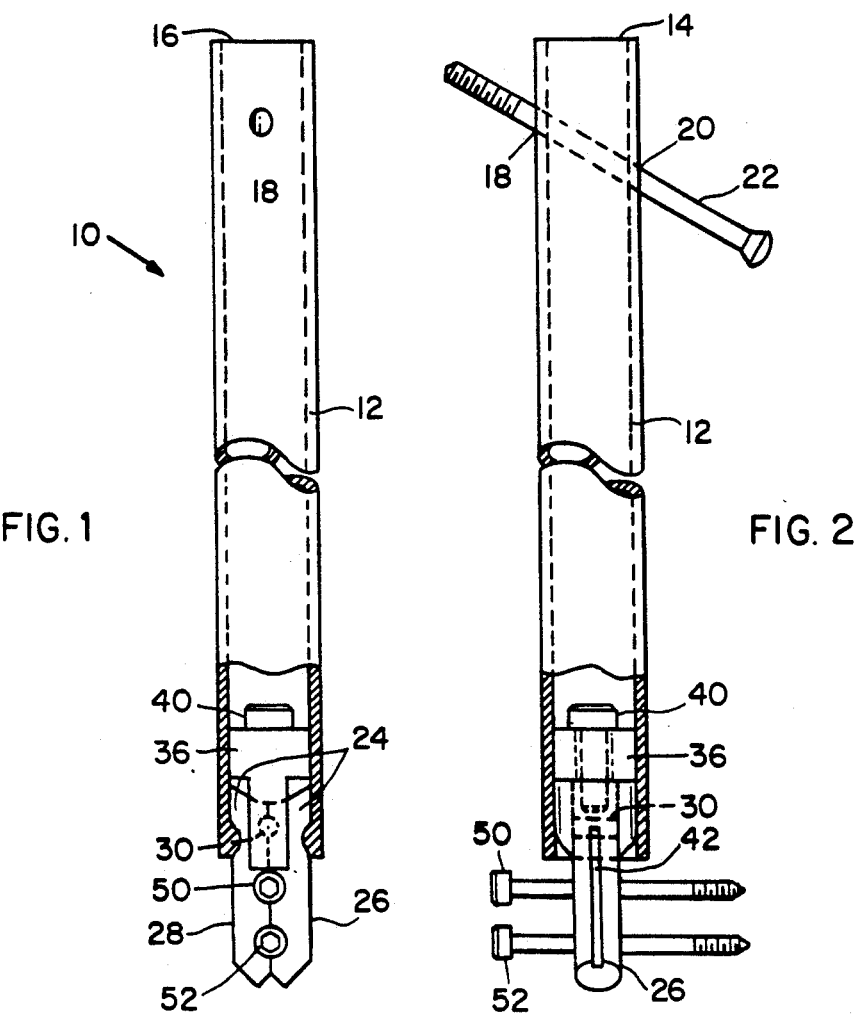
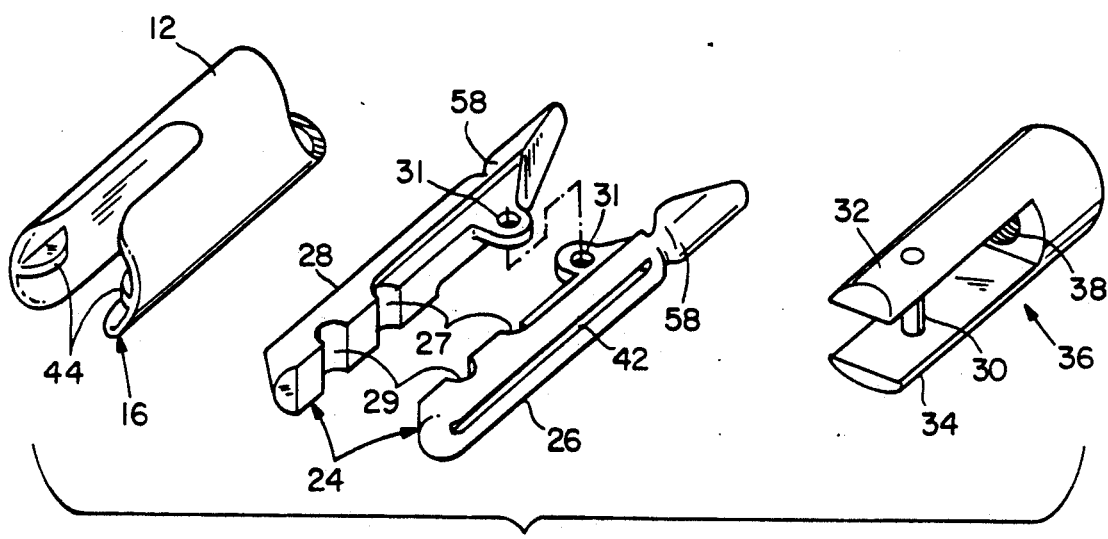

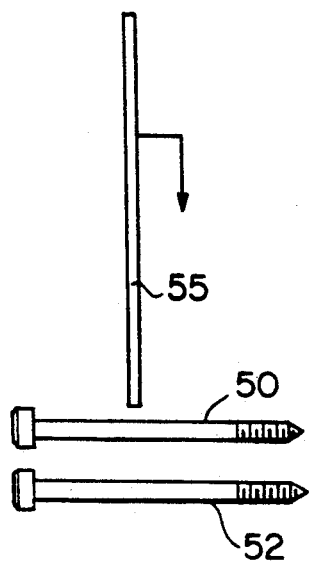
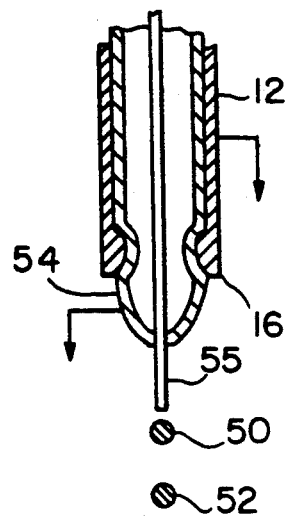
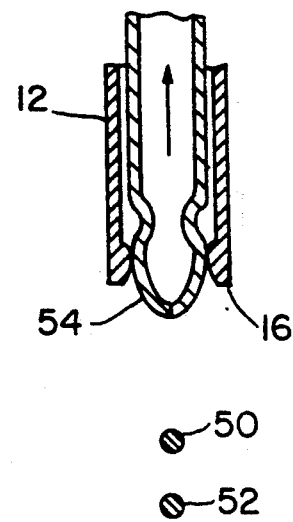
FIG. 4　　　　　FIG. 5　　　　　FIG. 6
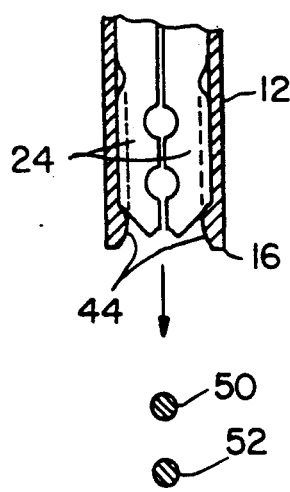
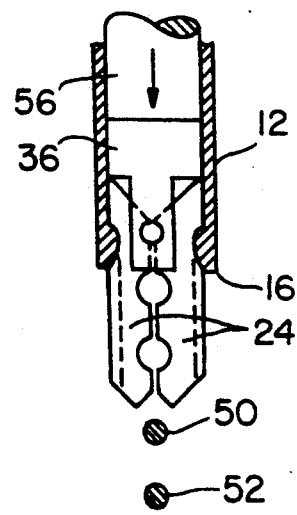
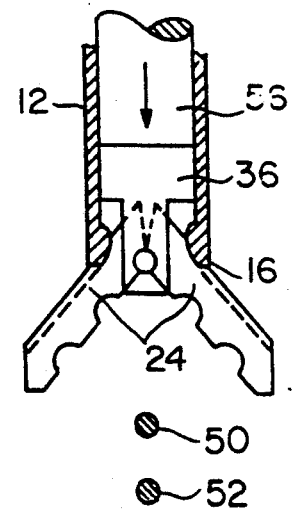
FIG. 7　　　　　FIG. 8　　　　　FIG. 9

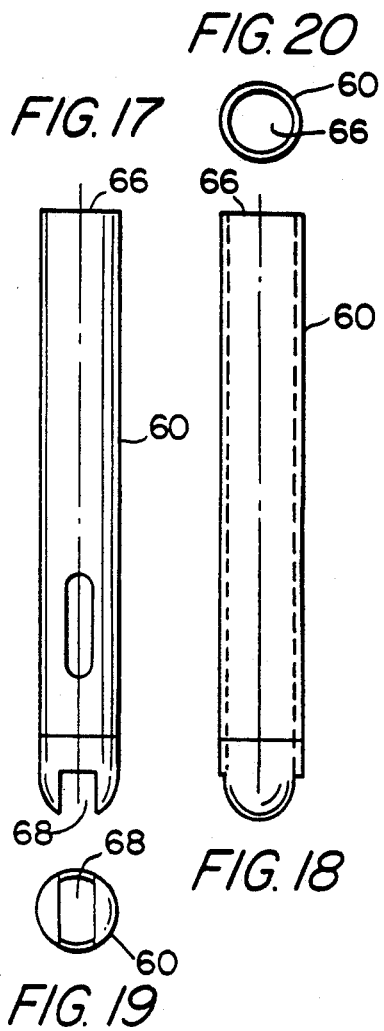
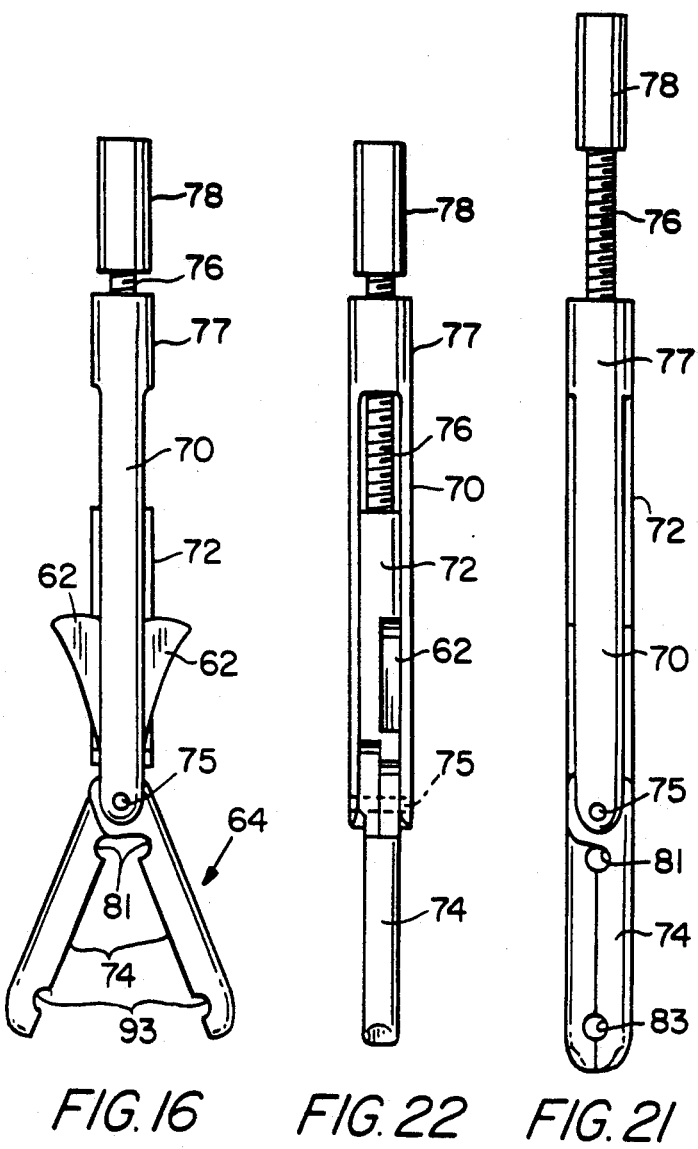
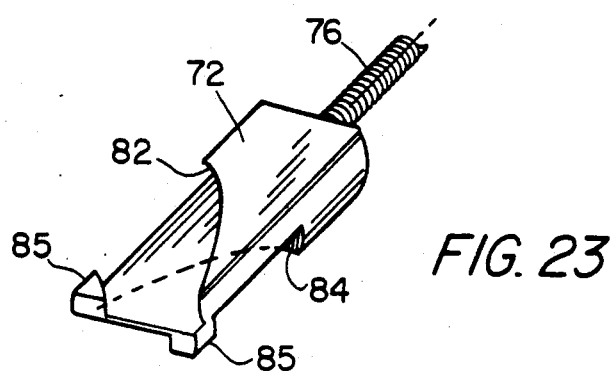

INTRAMEDULLARY NAIL

BACKGROUND OF THE INVENTION

This invention relates to an intramedullary nail structure and to a method for positioning the intramedullary nail in a bone structure.

A severe fracture in a long bone of the arm or leg such as the tibia or femur bone has a tendency to cause the bone segments created by the fracture to compress, thereby, shortening the length of the bone or mispositioning the bone due to torsion. Presently, a cannulated intramedullary nail that is inserted into an opening made in one end of the bone and passed through the medullary canal past the points of fracture is used to avert such compression or torsion. A guide wire is first inserted in the opening usually made in the proximal end of the bone, and into the distal bone fragment significantly past the fracture sites. The guide wire guides the cannulated nail past the fracture sites. Although the intramedullary nail substantially occupies the medullary canal, it is only capable of retaining length and preventing excessive bone shortening if the bone segments are appropriately fastened, or locked, to the nail.

The major problem in using a locked intramedullary nail is locating distal aperture(s) in the nail and successfully aligning fasteners, inserted through the bone wall, with the apertures. The use of a jig has been proposed that is accurately retained in relationship to the nail by a portion extending into the bone through the proximal opening in the bone and which has an external portion that extends parallel the bone. Alignment means are provided for aligning the fasteners with the apertures in the nail along the external portion. While such a technique is successful at accurately locating the proximal locking fastener(s), the long distance to the distal fasteners from the proximal end of the bone allows relative movement between the jig and the nail which distorts the alignment means. Accordingly, alignment with the distal aperture(s) is not assured and damage to the bone wall or to the nail aperture may result.

A more accurate technique for locating distal apertures is an X-ray imaging technique that utilizes a target device. The target device is positioned at the approximate location of the distal nail aperture and iteratively repositioned until a perfect circular image of the nail aperture is produced. This occurs when the target device is located on the center line of the aperture. Means are provided, relative to the target device, to then locate the insertion point for the fasteners. The problem with such a distal aperture location technique is the cumulative exposure of the patient and the operating team to X-ray radiation which can be excessive if the procedure to properly position the target device requires excessive time. It is also less than precise due to optical deformation and wrong perspective of the image.

It has been proposed in U.S. Pat. Nos. 4,705,027 and 4,817,591 to provide an intramedullary nail having a distal tip with a slot which engages a screw previously inserted through a distal portion of a bone. Such an intramedullary nail also is disclosed in U.S. Pat. No. 4,846,162. Other intramedullary devices such as nails are disclosed in U.S. Pat. Nos. 2,381,050; 3,216,414; 4,498,468; 4,827,917; 4,805,607; 4,913,137 and 51057,103.

While nails having a fixed slot which engages a previously introduced screw or stud into a distal end of a bone have been proposed, they are difficult to use. The slot utilized is small. That is, it has a cross-section dimension less than the horizontal cross-sectional area of the nail. Therefore, it is difficult to align properly with a small screw or stud previously positioned in the bone transverse to the nail. Such difficulties also arise because the nail may become rotated about its vertical axis during insertion through the medullar canal. In addition, the nail surrounds only a portion of the circumference of the screw or stud so that it is free to move relative to the screw or stud.

Accordingly, it would be desirable to provide an intramedullary nail which can be properly positioned quickly to minimize patient exposure to radiation. In addition, it would be desirable to provide such a nail which can be positioned to surround one or more mating fasteners and which can be subsequently removed easily.

SUMMARY OF THE INVENTION

In accordance with this invention an intramedullary nail is provided with expandable jaws at its distal end. The jaws are configured to clamp about one or more fixed distal fasteners such as studs or screws which are inserted into the broken long bone prior to or subsequent to inserting the nail through the medullar canal. The expandable jaws provide the substantial advantage of providing a large space into which the fasteners can be positioned and renders the fasteners much more easily to target for proper positioning of the nail. The nail includes a hollow guide tube through which the jaws are inserted and a guide means at the distal end which functions to open the jaws and to close the jaws about the fasteners. The jaws, when closed can be locked into place about the fasteners and can be subsequently unlocked so that the fasteners and jaws can be removed after the broken bone has healed. The fasteners are located by the jaws when they are in an expanded position. The increased distance between the two arms forming the jaws facilitates properly locating the distal fasteners as compared with a nail having a fixed slot of a size to snugly fit about a preset fasteners. A fixed slot has a reduced bite range as compared to the expandable jaws utilized in the present invention, particularly when commonly encountered nail rotation occurs when the nail is inserted through the medullar canal. When the jaws are contracted about the fasteners, the nail can assist in reversing its rotation so that it is properly positioned.

BRIEF DESCRIPTION OF THE DRAWINGS

FIG. 1 is a front view of the intramedullary nail of this invention.

FIG. 2 is a side view of the nail of FIG. 1.

FIG. 3 is a partial exploded view of the jaws portion of the nail of this invention.

FIGS. 4–15 illustrate the sequence of use of the nail of this invention.

FIG. 16 is a front view of an alternative structure of this invention with jaws in an open position.

FIG. 17 is a side view of a sleeve utilized with the structure of FIG. 16.

FIG. 18 is a cross-sectional view of the sleeve of FIG. 17.

FIG. 19 is a bottom view of the sleeve of FIG. 17.

FIG. 20 is a top view of the sleeve of FIG. 17.

FIG. 21 is a front view of the structure of FIG. 16 with the jaws closed.

FIG. 22 is a side view of the structure of FIG. 21.

FIG. 23 is a perspective view of a drive bracket utilized in the structure of FIG. 16.

DESCRIPTION OF SPECIFIC EMBODIMENTS

Figure 10:
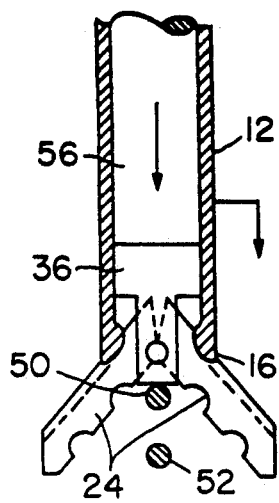

The nail of this invention comprises a hollow stem which extends the length of the bone being treated such as the femur or tibia which is to be set for healing. The top end of the stem is provided with an opening through which a fixed support such as a screw or stud can be positioned after the nail is properly aligned in the medullar canal. The distal end of the nail is provided with a set of jaws formed by two arms pivotally mounted within or adjacent the distal end of the stem. The jaws cooperate with the fixed supports in the distal end of the stem. The jaws can be moved axially through the stem so that the jaws are positioned outside of and adjacent to the distal end of the stem either in an open or closed position. In use, one or more fixed supports or fasteners are set through the distal end of the bone being treated, transversely through the medullar canal. When more than one distally positioned fasteners is utilized, they are set at different vertical heights but oriented in the same direction. The hollow stem portion of the nail is positioned within the medullar canal so that its distal end is adjacent the distally positioned fixed support(s). A portion of the apparatus adjacent the pivot for the jaws contacts the distal support nearest the stem so that openings in the arms of the jaws can be extended around the distal supports when the jaws are closed. Means are provided for setting the jaws in a closed position which means, can be subsequently removed. Later the means can be reinserted to loosen the jaws and facilitate removal of the jaws, nail and fixed supports subsequent to bone healing.

The nail of this invention includes expandable and contractible jaws. When in an expanded position, the expanded space between the jaws greatly enhances the proper positioning of the nail about one or more fasteners or studs positioned at a distal end of the nail. In addition, when the jaws are contracted about the fasteners, proper positioning of the nail is enhanced. In the smaller bones, the fasteners adjacent the distal end of the nail need not be employed. The nail is maintained in position by expanding the jaws which effect proper positioning by frictional forces of the jaws against the inner wall of the bone. In this embodiment, slots accommodating fasteners need not be included. The apparatus of this invention will be described below with reference to the figures by way of example.

Referring to FIGS. 1, 2 and 3, the nail 10 in one embodiment of this invention includes a hollow stem 12 having a top end 14 and an distal end 16. The top end 14 is provided with two holes 18 and 20 so that a screw or stud 22 can be inserted through the stem 12 adjacent the top end 14.

A set of jaws 24 is formed of two arms 26 and 28 which are pivotally mounted on pivot 30 through holes 31. The arms 26 and 28 are provided with grooves 27 and 29 which fit around screws 50 and 52. Pivot 30 is fixed between two guide arms 32 and 34 which are part of guide 36. Guide 36 is provided with a hole 31 which accommodates a means for maintaining the jaws 24 closed such as a set screw 40. The jaws can be provided with a guide slot 42 on each arm 26 and 28. The distal end 16 of stem 12 is provided with guides 44 which fit into guide slots 42. The guides 44 and guide slots 42 cooperate to effect opening and closing of the jaws in a manner which will be more fully discussed below.

Figure 11:
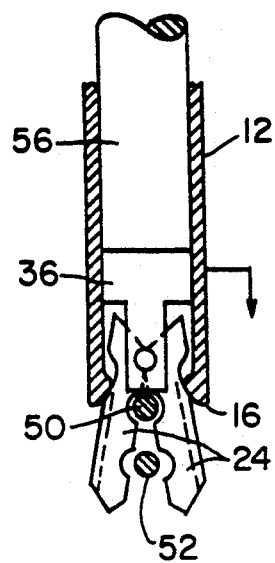
Figure 12:
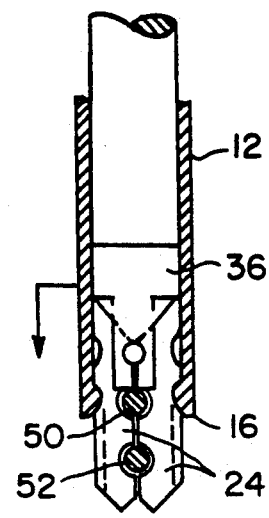
Figure 13:
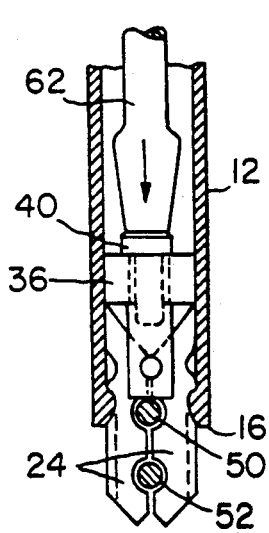
Figure 14:
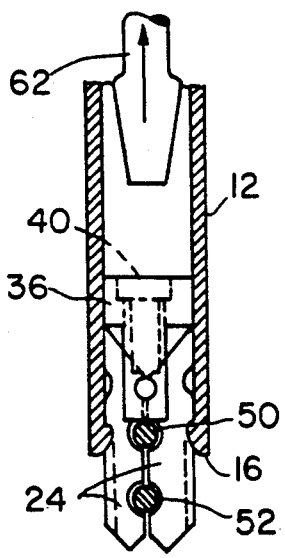
Figure 15:
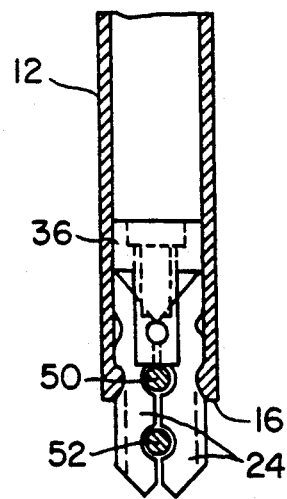

Referring to FIGS. 4 through 15, a description of the functioning of the nail of this invention is provided. In a first step as depicted in side view FIG. 4 and front view, FIG. 5, locating top screw 50 and bottom screw 52 are established at the distal end of a bone to be healed. The stem 12 contains a penetration tip 54, which in turn follows a guide wire 55 which extends a known distance from the proximal end 14 of the stem 12 past the distal end 16. This distance is long enough to permit the jaws 24 to be opened but sufficiently close to the emplacement of the screw 50 so that the jaws can be closed about the screws 50 and 52 quickly and easily. The end of the guide wire 55 is used to determine the location of the top screw 50. After the location of the top screw 50 has been determined with the guide wire 55 and the stem properly positioned, the guide wire 55 and penetration tip 54 are withdrawn, as depicted in FIG. 6, through the top end 14 of the stem 12. As shown in FIG. 7, the jaws 24 are inserted through stem 12 in a rotational position so that the guides 44 pass through the guide slots 42. Insertion is effected with a downwardly moved guide rod 56 which is screwed onto side guide 36 to the positions depicted in FIGS. 7 and 8. The jaws 24 are opened as shown in FIG. 9 by depressing them further with guide rod 56 until guides 44 contact shoulders 58 on arms 26 and 28. This contact causes the portion of arms 26 and 28 above the pivot 30 to compress toward each other and to open the jaw 24 as shown in FIGS. 9 and 10. The stem 12 then is moved further downward with the jaws 24 open until the side guide 36 contacts the top screw 50 as shown in FIG. 10. As shown in FIG. 11, after contact with screw 50 is effected, the stem 12 is moved further downward so that guides 44 enter guide slots 42 which causes the jaws 24 to begin to close. Guide arms 32 and 34 maintain contact with screw 50 while letting stem 12 slide downwards effects retention of jaws 29 in place. Stem 12 sheaths the jaws 24 thus closing them. In an alternative embodiment, the guides can be located on the arms and the guide slots can be located on the distal end of the stem. As shown in FIG. 11, movement of the stem 12 downwardly is stopped when the jaws 24 have closed completely about the screws 50 and 52. The guide rod 56 is removed from the stem 12 and a set screw 40 is positioned between the arms 26 and 28 above the pivot 30. The screw driver 62 then is removed as shown in FIG. 14 to effect the position shown in FIG. 15.

Subsequent to healing, the set screw 40 is removed, the screws 50 and 52 are removed. The stem 12 and jaws 24 then are raised to remove them from the medullar canal.

Referring to FIGS. 16 through 20, hollow stem 60 is shown which is useful in a second embodiment of the nail 61 of this invention. The stem 60 includes two slots 59 through which arms 62 extend when jaw 64 is open.

The stem 60 has an open top 66 and a bottom slot 68. The nail 61 includes a housing 70 for a drive bracket 72 and for jaws 74 mounted on a pivot 75. A screw 76 is mounted through top section 77 of housing 70 and is attached at one end to head 78 and at a second end to drive bracket 72. The jaws 74 include slots 81 and 83 to accomodate fasteners.

Figure 27:
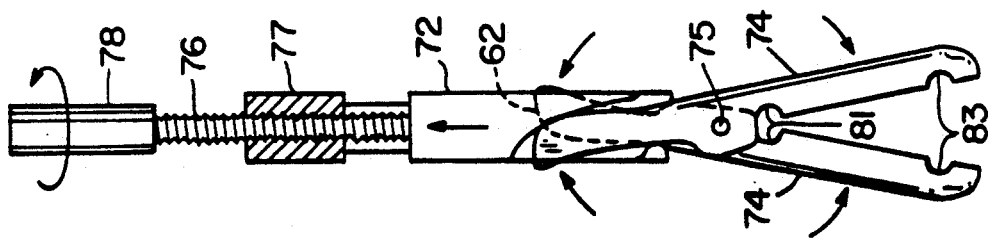
FIG. 27 illustrates the closing mechanism of the structure of FIG. 25.
Figure 26:
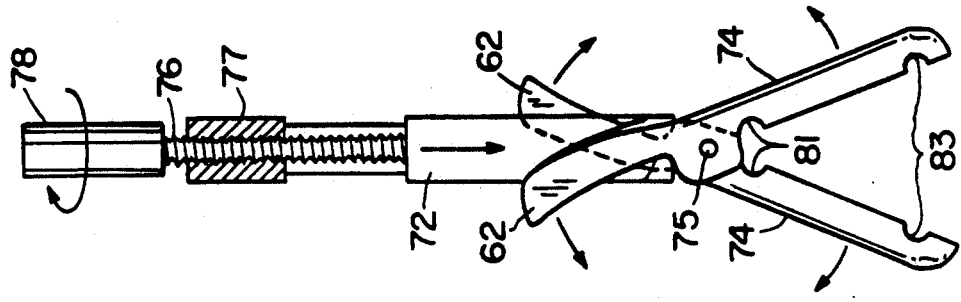
FIG. 26 illustrates the opening mechanism of the structure of FIG. 25.
Figure 25:
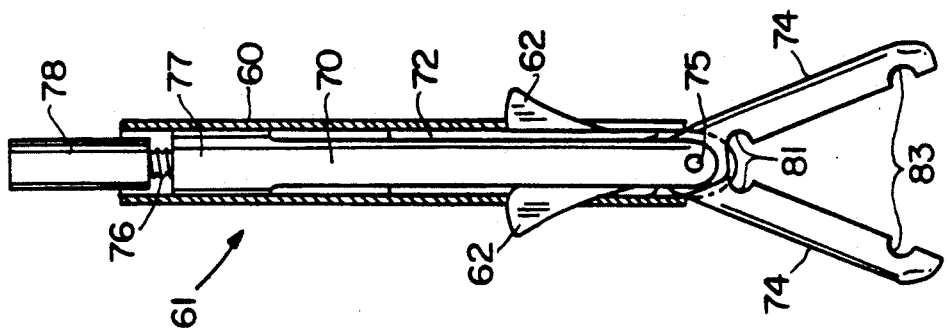
FIG. 25 is a cross-sectional view showing the assembly of the structures of FIGS. 16 and 17.
Figure 24:
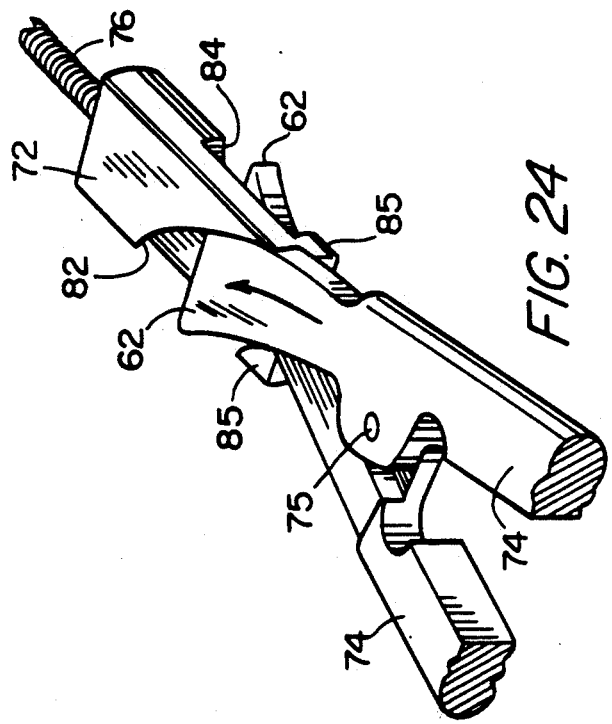
FIG. 24 illustrates the engagement of the drive bracket of FIG. 23 with the expandable jaws in the structure of FIG. 16.

As shown in FIGS. 23 and 24, the drive bracket 72 includes two curved faces 82 and 84 which contact arms 62. Arm 62 also contact detents 85. As shown in FIG. 26, when head 78 and screw 76 are rotated clockwise, the drive bracket 72 moves downwardly and causes the arms 62 and jaws 74 to open. As shown in FIG. 27, when head 78 and screw 76 are rotated counterclockwise, the drive bracket 72 moves upwardly and causes arms 62 and jaws 74 to close because of detent 85.

We claim:

1. An intramedullary nail to stabilize fractured bone fragments comprising a hollow stem having an upper end and a distal end, said upper end having a pair of holes to accommodate a fixed support extending through walls of the stem, a set of jaws positioned within said hollow stem, said jaws formed of pivotally mounted arms positioned at and extending outwardly from said distal end, means extending through said stem for moving said jaws between an open jaw position and a closed jaw position and groove means on said arms having a size to accommodate in said closed jaw position at least one distal fixed support extending through a fractured bone.

2. The nail of claim 1 wherein said jaws are adapted to accommodate a plurality of fixed supports.

3. The nail of claim 2 wherein said means for fixing said arms about said at least one fixed distal support comprises a set screw.

4. The nail of claim 1 wherein said jaws are moved by means of mating guides in slidable contact with guide slots, either said guides or said guide slots being attached to a pivot arm to which said arms are attached and the other of said guides or said guide slots being attached to said means extending through said stem.

5. The nail of claim 4 wherein said guides are attached to said pivot.

6. The nail of claim 4 wherein said guides slots are attached to said pivot.

7. The process of fixing an intramedullary nail within a medullar canal of a fractured bone which comprises inserting at least one fixed support adjacent a distal end of a fractured bone and transverse to said canal, passing a hollow stem of said nail through said canal to a position adjacent said at least one fixed support, passing jaws having pivotally mounted arms through said hollow stem, expanding said jaws to position said jaws around said at least one fixed support, contracting said jaws to secure said jaws to said at least one fixed support and setting said jaws in the contracted position.

8. The process of claim 7 wherein said jaws are set about a plurality of fixed supports adjacent said distal end.

9. The process of claim 8 wherein a top end of said stem is fixed into position subsequent to setting said jaw.

10. The process of claim 7 wherein a top end of said stem is fixed into position subsequent to setting said jaw.

11. An intramedullary nail to stabilize fractured bone fragments comprising a hollow stem having an upper end and a distal end, said upper end having a pair of holes to accommodate a fixed support extending through walls of the stem, a set of jaws positioned within said hollow stem, said jaws formed of pivotally mounted arms positioned at and extending outwardly from said distal end, a drive bracket extending through said stem, said drive bracket having detent means and two curved surfaces positioned to contact said arms, said curved surfaces shaped to effect opening or closing of said arms when said surfaces are moved relative to said arms within said stem, said detent means positioned to control the extent of opening or closing of said arms when moved relative to said arms within said stem and groove means on said arms having a size to accommodate in said closed jaw position at least one distal fixed support extending through said fractured bone.

* * * * *